US006520971B1

(12) United States Patent
Perry et al.

(10) Patent No.: US 6,520,971 B1
(45) Date of Patent: Feb. 18, 2003

(54) FULL THICKNESS RESECTION DEVICE CONTROL HANDLE

(75) Inventors: Stephen J. Perry, Shirley, MA (US); Paul DiCesare, Easton, CT (US); Patrick Gutelius, Monroe, CT (US); Mark Monroe, Holliston, MA (US); Jeffrey Radziunas, Wallingford, CT (US)

(73) Assignee: Scimed Life Systems, Inc., Maple Grove, MN (US)

( * ) Notice: Subject to any disclaimer, the term of this patent is extended or adjusted under 35 U.S.C. 154(b) by 212 days.

(21) Appl. No.: 09/722,026

(22) Filed: Nov. 27, 2000

(51) Int. Cl.$^7$ ............................................. A61B 17/10
(52) U.S. Cl. ...................................................... 606/139
(58) Field of Search ................................ 606/139, 219, 606/75; 600/131; 227/175.1, 180.1

(56) References Cited

U.S. PATENT DOCUMENTS

| | | |
|---|---|---|
| 1,185,292 A | 5/1916 | Astafiev |
| 2,905,178 A | 9/1959 | Hilzinger, III |
| 3,193,165 A | 7/1965 | Akhalaya et al. |
| 3,388,847 A | 6/1968 | Kasulin et al. |
| 3,452,615 A | 7/1969 | Gregory, Jr. |
| 3,552,626 A | 1/1971 | Astafiev |
| 3,638,652 A | 2/1972 | Kelley |
| 3,952,747 A | 4/1976 | Kimmell, Jr. |
| 4,047,654 A | 9/1977 | Alvarado |
| 4,108,211 A | 8/1978 | Tanaka |
| 4,155,452 A | 5/1979 | Wetterman et al. |
| 4,198,982 A | 4/1980 | Fortner et al. |
| 4,207,898 A | 6/1980 | Becht |
| 4,211,229 A | 7/1980 | Wurster |
| 4,261,346 A | 4/1981 | Wettermann |
| 4,285,376 A | 8/1981 | Ausnit |
| 4,304,236 A | 12/1981 | Conta et al. |

(List continued on next page.)

FOREIGN PATENT DOCUMENTS

| | | |
|---|---|---|
| DE | 2 347 418 | 9/1973 |
| EP | 0 442 588 A2 | 8/1991 |
| GB | 2 016 991 A | 10/1979 |
| GB | 2 038 692 A | 7/1980 |
| WO | WO 93/15668 | 8/1993 |
| WO | WO 96/18344 | 6/1996 |

OTHER PUBLICATIONS

Waxman, Bruce et al., "Stapling in Colorectal Surgery," Surgery of the Colon, Rectum and Anus, W.B. Saunders Co., Philadelphia, 1995, pp. 778–811.

Swain, C. Paul et al., "An Endoscopic Stapling Device: the Development of a New Flexible Endoscopically Controlled Device for Placing Multiple Transmural Staples in Gastrointestinal Tissue," Gastrointestinal Endoscopy, American Society of Gastrointestinal Endoscopy, vol. 35, No. 4, 1989, pp. 338–339.

(List continued on next page.)

Primary Examiner—John J. Calvert
Assistant Examiner—James G Smith
(74) Attorney, Agent, or Firm—Fay Kaplun & Marcin, LLP

(57) ABSTRACT

A control handle for a full thickness resection device is disclosed. In an embodiment for the control handle of the present invention, the control handle includes a body and a staple firing assembly coupled to the body. The staple firing assembly includes a rotatable staple firing ring, a worm gear assembly rotatably engaged with the staple firing ring, and a flexible drive shaft coupled to the worm gear assembly. In an embodiment for a method of the present invention, a method for actuating a full thickness resection device is provided. The method includes the steps of rotating a staple firing ring in a first direction and actuating a worm gear assembly in a first operative mode in response to the rotation of the staple firing ring in the first direction, the worm gear assembly is coupled to the staple firing ring. A flexible drive shaft is rotated in the first direction, the flexible drive shaft being coupled to the worm gear assembly, and torsional energy is stored in the flexible drive shaft during rotation of the flexible drive shaft in the first direction. The worm gear assembly is actuated in a second operative mode and a release rate of the stored torsional energy in the flexible drive shaft is controlled by the worm gear assembly. The flexible drive shaft is rotated in a second direction.

21 Claims, 4 Drawing Sheets

U.S. PATENT DOCUMENTS

| | | |
|---|---|---|
| 4,319,576 A | 3/1982 | Rothfuss |
| 4,351,466 A | 9/1982 | Noiles |
| 4,473,077 A | 9/1984 | Noiles et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,610,383 A | 9/1986 | Rothfuss et al. |
| 4,617,928 A | 10/1986 | Alfranca |
| 4,632,290 A | 12/1986 | Green et al. |
| 4,646,722 A | 3/1987 | Silverstein et al. |
| 4,667,673 A | 5/1987 | Li |
| 4,671,445 A | 6/1987 | Barker et al. |
| 4,716,900 A | 1/1988 | Ravo et al. |
| 4,741,326 A | 5/1988 | Sidall et al. |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,841,968 A | 6/1989 | Dunn et al. |
| 4,880,015 A | 11/1989 | Nierman |
| 4,886,049 A | 12/1989 | Darras |
| 4,893,622 A | 1/1990 | Green et al. |
| 4,907,591 A | 3/1990 | Vasconcellos et al. |
| 4,957,499 A | 9/1990 | Lipatov et al. |
| 5,005,749 A | 4/1991 | Aranyi |
| 5,009,643 A | 4/1991 | Reich et al. |
| 5,014,899 A | 5/1991 | Presty et al. |
| 5,015,249 A | 5/1991 | Nakao et al. |
| 5,025,778 A | 6/1991 | Silverstein et al. |
| 5,049,153 A | 9/1991 | Nakao et al. |
| 5,100,419 A | 3/1992 | Ehlers |
| 5,100,420 A | 3/1992 | Green et al. |
| 5,122,156 A | 6/1992 | Granger et al. |
| 5,139,513 A | 8/1992 | Segato |
| 5,156,609 A | 10/1992 | Nakao et al. |
| 5,158,222 A | 10/1992 | Green et al. |
| 5,171,222 A | 12/1992 | Euteneuer et al. |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,219,111 A | 6/1993 | Bilotti et al. |
| 5,222,963 A | 6/1993 | Brinkerhoff et al. |
| 5,251,801 A | 10/1993 | Ruckdeschel et al. |
| 5,258,008 A | 11/1993 | Wilk |
| 5,259,366 A | 11/1993 | Reydel et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,314,435 A | 5/1994 | Green et al. |
| 5,314,436 A | 5/1994 | Wilk |
| 5,328,077 A | 7/1994 | Lou |
| 5,330,486 A | 7/1994 | Wilk |
| 5,333,773 A | 8/1994 | Main et al. |
| 5,344,059 A | 9/1994 | Green et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,395,034 A | 3/1995 | Allen et al. |
| 5,403,333 A | 4/1995 | Kaster et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,441,507 A | 8/1995 | Wilk |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,465,895 A | 11/1995 | Knodel et al. |
| 5,474,223 A | 12/1995 | Viola et al. |
| 5,484,451 A | 1/1996 | Akopov et al. |
| 5,485,947 A | 1/1996 | Olson et al. |
| 5,485,952 A | 1/1996 | Fontayne |
| 5,522,534 A | 6/1996 | Viola et al. |
| 5,533,661 A | 7/1996 | Main et al. |
| 5,571,116 A | 11/1996 | Bolanos et al. |
| 5,609,285 A | 3/1997 | Grant et al. |
| 5,749,893 A | 5/1998 | Vidal et al. |
| 5,868,760 A | 2/1999 | McGuckin, Jr. |
| 6,119,913 A | 9/2000 | Adams et al. |
| 6,126,058 A | 10/2000 | Adams et al. |

OTHER PUBLICATIONS

Swain C. Paul et al., "Knot Tying at Flexible Endoscopy," Gastrointestinal Endoscopy, American Society of Gastrointestinal Endoscopy, vol. 40, No. 6, 1994, pp. 722–729.

Swain C. Paul et al., "An Endoscopic Sewing Machine," Gastrointestinal Endoscopy, American Society of Gastrointestinal Endoscopy, vol. 32, No. 1, 1986, pp. 36–38.

Swain C. Paul et al., "An Endoscopically Deliverable Tissue–Transfixing Device for Securing Biosensors in the Gastrointestinal Tract," Gastrointestinal Endoscopy, American Society of Gastrointestinal Endoscopy, vol. 40, No. 6, 1994, pp. 730–734.

Escourrou, J. et al., "First Clinical Evaluation and Experimental Study of a New Mechanical Suture Device for Endoscopic Hemostasis," Gastrointestinal Endoscopy, American Society of Gastrointestinal Endoscopy, vol. 36, No. 5, 1990, pp. 494–497.

Pietrafitta, Joseph J. et al., "Experimental Transperitoneal Laparoscopic Pyloroplasty," Surgical Laparoscopy & Endoscopy, Raven Press, Ltd., New York, vol. 2, No. 2, 1992, pp. 104–110.

Hiller, Joe A., "Surgical Stapling Techniques," Ethicon a Johnson & Johnson Company, 1986.

FULL THICKNESS RESECTION DEVICE CONTROL HANDLE

BACKGROUND OF THE INVENTION

1. Field of the Invention

The present invention relates generally to a full thickness resection device. More specifically, the invention provides a control handle for a full thickness resection device.

2. Description of the Related Art

Full thickness resection devices are known. Resection devices are capable of removing a lesion from the patient's body by stapling and cutting the lesion site. Since it is desirable to perform the resection procedure endoscopically through a naturally occurring body orifice, the resection device may include a flexible shaft extending from the operating end, or distal end, of the device, which is inserted into the patient's body, to the control end, or proximal end, of the device, which remains outside of the patient's body. The control end includes a control handle which is used to control the cutting and stapling apparatuses of the device.

Because the resection device includes a flexible shaft, a portion of the apparatus that controls the cutting and stapling apparatus, e.g., that portion of the device that extends from the control handle to the distal end of the device through the flexible shaft, may also be formed of a flexible material. This flexible portion may be a flexible drive shaft that is used to transmit an actuating force from the control handle to the operating, or distal, end of the device. For example, the flexible drive shaft could be rotated in a first direction to actuate the stapling apparatus and rotated in a second direction, which is opposite to the first direction, to actuate the cutting apparatus. In such an embodiment, the drive shaft could be coupled to the stapling apparatus at its distal end and cause the staples to be fired from the stapling apparatus as the drive shaft is rotated in a clockwise direction. At completion of its clockwise rotation, the distal end of the flexible drive shaft could couple with the cutting apparatus and could cause the targeted tissue to be cut as the drive shaft is rotated in a counter-clockwise direction.

However, problems could be encountered with an embodiment of a device as described above. Because the drive shaft that couples the control handle of the device to the distal end of the device is flexible, as the drive shaft is rotated in the clockwise direction, the drive shaft will not only be rotated by the rotation force but the shaft will most likely store torsional energy in it as well. When the force that caused the drive shaft to rotate in the clockwise direction is removed from the drive shaft, the drive shaft will tend to uncontrollably rotate in the counter-clockwise direction due to the uncontrolled release of the torsional energy that was stored in the drive shaft. This could have undesirable consequences since the counter-clockwise rotation of the drive shaft causes cutting of the targeted tissue. Uncontrolled release of the torsional energy stored in the drive shaft could result in complications in the cutting procedure.

Therefore, it would be desirable to provide an improved apparatus and method for a control handle of a full thickness resection device that could more positively control the actuation of the operating end of the resection device.

SUMMARY OF THE INVENTION

A control handle for a full thickness resection device is provided. In an embodiment for the control handle of the present invention, the control handle includes a body and a staple firing assembly coupled to the body. The staple firing assembly includes a rotatable staple firing ring, a worm gear assembly rotatably engaged with the staple firing ring, and a flexible drive shaft coupled to the worm gear assembly.

In an embodiment for a method of the present invention, a method for actuating a full thickness resection device is provided. The method includes the steps of rotating a staple firing ring in a first direction and actuating a worm gear assembly in a first operative mode in response to the rotation of the staple firing ring in the first direction, the worm gear assembly is coupled to the staple firing ring. A flexible drive shaft is rotated in the first direction, the flexible drive shaft being coupled to the worm gear assembly, and torsional energy is stored in the flexible drive shaft during rotation of the flexible drive shaft in the first direction. The worm gear assembly is actuated in a second operative mode and a release rate of the stored torsional energy in the flexible drive shaft is controlled by the worm gear assembly. The flexible drive shaft is rotated in a second direction.

BRIEF DESCRIPTION OF THE DRAWINGS

The various features of the invention will best be appreciated by simultaneous reference to the description which follows and the accompanying drawings, in which.

DETAILED DESCRIPTION

Figure 1:
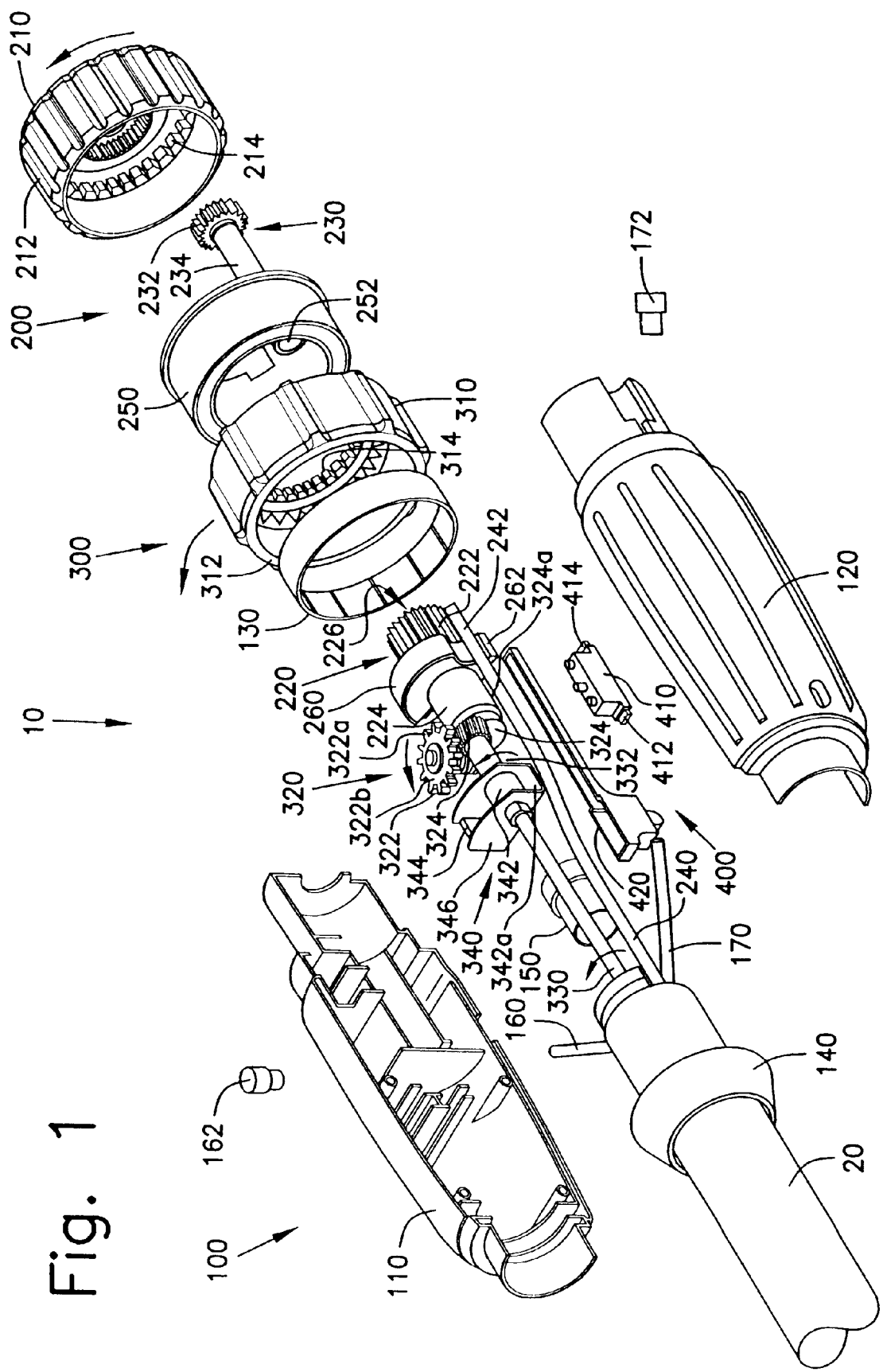
FIG. 1 is an exploded perspective view of an embodiment of the full thickness resection device control handle of the present invention.

FIGS. 1 through 5 illustrate an embodiment for the control handle 10 of the present invention. As can be seen, control handle 10 includes a body 100, a gap adjust assembly 200, a staple firing assembly 300, and a locking assembly 400. Each of these components will be discussed in further detail below.

Control handle 10 is disposed at a proximal end of a full thickness resection device where the proximal end is defined as that end which is located outside of the body of the patient. A flexible tube 20 extends from control handle 10 to the distal end of the full thickness resection device which includes the cutting and stapling apparatuses which are inserted into the body of a patient. Full thickness resection devices are well-known in the art and, thus, no further description of a full thickness resection device will be provided.

As will be described further later in this specification, control handle 10 includes mechanisms for adjusting the gap between the staple head and anvil head and for actuating the stapling and cutting apparatus, both of which are located at the distal end of the full thickness resection device.

As was mentioned above, control handle 10 includes a body 100 that is comprised of a first handle half 110 and a second handle half 120. The other components mentioned above which are included as part of control handle 10 are either disposed within body 100 or are coupled to body 100.

As can be seen, the internal structure of body 100 includes molded support framing which supports the components that are disposed within the body. As can be understood, first handle half 110 is joined to second handle half 120 with the components that are included within body 100 disposed between the first handle half 110 and the second handle half 120. A circular handle clamp ring 130 is disposed around the proximal ends of the handle halves 110, 120 and assist in maintaining the joined configuration for the two handle halves. Similarly, nose ring 140 is disposed around the distal ends of handle halves 110, 120 and also assist in maintaining the joined configuration for the two handle halves.

A scope seal 150 is disposed within body 100 and is maintained in its position within body 100 by the internal framing structure that is associated with handle halves 110, 120. Scope seal 150 defines an aperture through it. An endoscope is positioned through the aperture defined by scope seal 150. The endoscope extends through other portions of control handle 10, as will described, and extends through flexible tube 20 to the distal end of the full thickness resection device. A tube is positioned on the distal end of scope seal 150. The tube extends through flexible tube 20. Thus, an endoscope is positioned through scope seal 150 and through the tube that extends through flexible tube 20. The purpose of scope seal 150 is to provide a seal around the endoscope such that, as the bowel of the patient is insulfated, the air pressure is sealed against traveling back up through flexible tube 20 past scope seal 150.

Also included in body 100 is first grasper tube 160 and second grasper tube 170. First grasper tube 160 extends through first handle half 10 and second grasper tube 170 extends through second handle half 120. Grasper devices (not illustrated) are able to be inserted through each of first grasper tube 160 and second grasper tube 170. First grasper seal 162 is positioned on the end of grasper tube 160 which extends outside of first handle half 110. Second grasper seal 172 is similarly positioned on the end of second grasper tube 170 which extends outside of second handle half 120. The grasper seals provide a seal such that no materials are able to pass out of the proximal ends of the grasper tubes.

A description will be now be provided of gap adjust assembly 200. Gap adjust assembly 200 is utilized to adjust the gap between the staple head and the anvil head that are located at the distal end of the full thickness resection device. Gap adjust assembly 200 includes a gap adjust ring, or clamp knob, 210, a clamp shaft gear 220, a spur gear, or open/close gear, 230, a gap adjust flexible drive shaft 240, a transition piece 250, and a follower 260. Each of these components will be described in further detail below.

Gap adjust ring 210 is a circular structure that includes an aperture therethrough. The endoscope, as discussed previously, is receivable through the aperture defined by gap adjust ring 210. Gap adjust ring 210 is rotatably mounted on body 100 and includes gear teeth 212 on an inner portion thereof. As will be described, gear teeth 212 engage with gear teeth 222 that are included on clamp shaft gear 220. Gap adjust ring 210 also includes cogs 214 that are also included on the inner portion of gap adjust ring 210. As will also be described later in this specification, cogs 214 receive within them locking assembly 400 which locks gap adjust ring 210 from being rotated when the locking assembly is received within one of cogs 214.

As was mentioned above, clamp shaft gear 220 includes gear teeth 222 on a portion of clamp shaft gear 220. As was also mentioned previously, gear teeth 222 of clamp shaft gear 220 engage with gear teeth 212 of gap adjust ring 210.

As can be understood, as gap adjust ring 210 is rotated, gear teeth 212, through engagement with gear teeth 222, rotate clamp shaft gear 220. Clamp shaft gear 220 also defines an aperture 226 therethrough which receives the endoscope through it.

Clamp shaft gear 220 also engages with spur gear 230. Thus, gear teeth 222 of clamp shaft gear 220 also engage with gear teeth 232 of spur gear 230. Thus, as can be understood, as gap adjust ring 210 rotates clamp shaft gear 220, clamp shaft gear 220 in-turn rotates spur gear 230. Thus, spur gear 230 is not directly driven by gap adjust ring 210, rather, spur gear 230 is indirectly driven by gap adjust ring 210 through rotation of clamp shaft gear 220 by gap adjust ring 210. This gearing mechanism for gap adjust assembly 200 is utilized for a variety of reasons including the position of the endoscope through the centerline of the control handle 10 and the desired drive ratio for the gap adjust ring 210 and the spur gear 230.

In further describing spur gear 230, shaft 234 of spur gear 230 extends through a slot 252 that is defined by transition piece 250. Thus, spur gear 230 is structurally supported by slot 252 in transition piece 250 and spur gear 230 is able to rotate within slot 252. The distal end of shaft 234 of spur gear 230 is connected to gap adjust flexible drive shaft 240. Thus, the proximal end 242 of gap adjust drive shaft 240 is attached to spur gear 230.

Proximal end 242 of drive shaft 240 is positioned within a scallop 262 which extends from follower 260. Scallop 262 allows for rotation of drive shaft 240 within scallop 262 and scallop 262 supports drive shaft 240 at its proximal end 242. As can be understood, as spur gear 230 is rotated by clamp shaft gear 220, drive shaft 240 is also rotated due to the rigid attachment between drive shaft 240 and spur gear 230.

Gap adjust drive shaft 240 is a flexible shaft and, thus, stores torsional energy within it as it is rotated. Drive shaft 240 extends distally from control handle 10 where the distal end (not shown) of drive shaft 240 is connected to a yoke in the distal end of the full thickness resection device. Rotation of drive shaft 240 translationally moves the yoke which in-turn positions the anvil head with respect to the staple head to adjust the stapling gap between the anvil head and the staple head.

Figure 2:
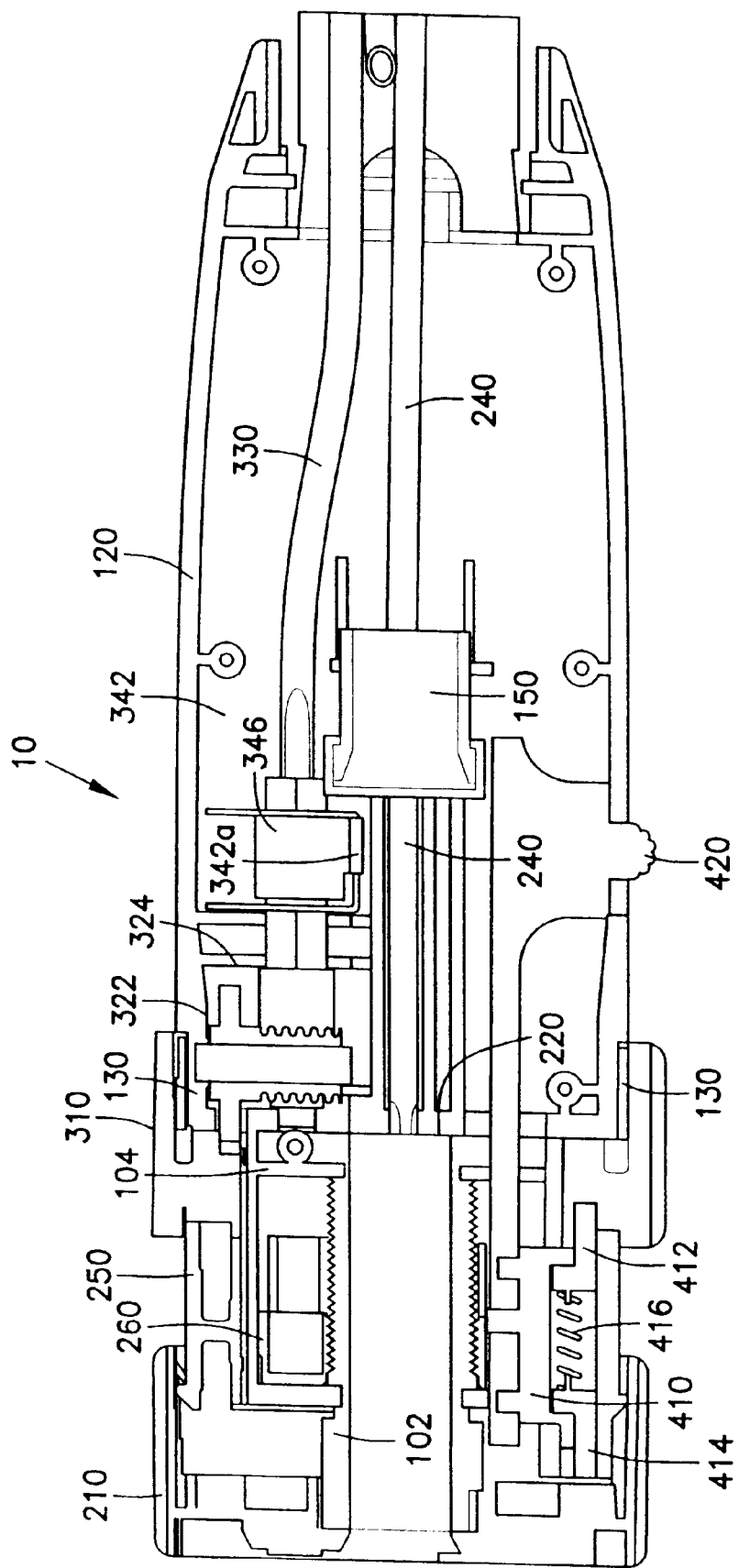
FIG. 2 is a cross-sectional view of the embodiment of FIG. 1.
Figure 3:
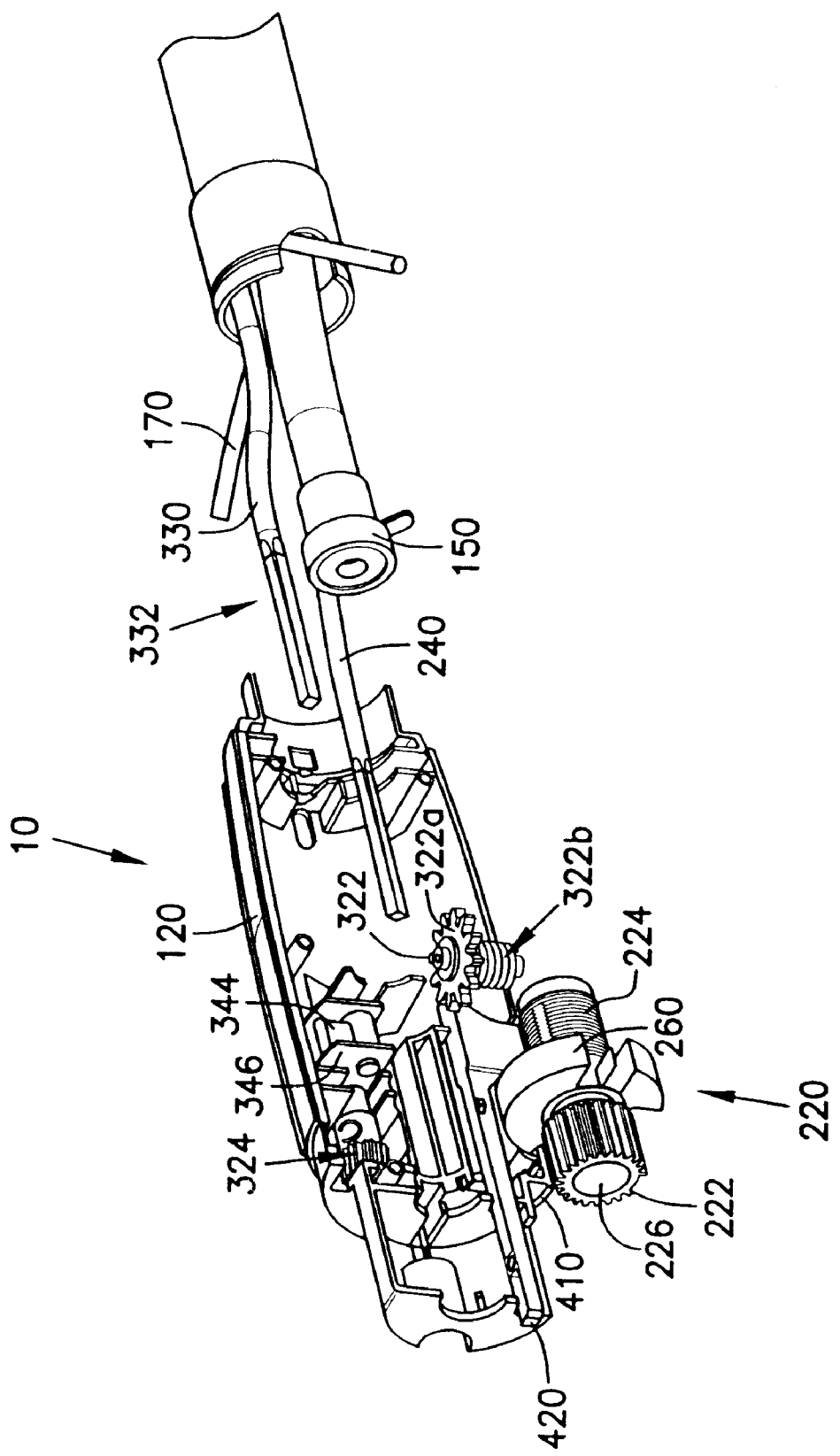
FIG. 3 is an exploded perspective view of a portion of the control handle of FIG. 1.

In further describing follower 260, the follower is movably disposed on clamp shaft gear 220. Follower 260 includes a threaded portion on an internal side thereof that engages with a threaded shaft 224 that is included on clamp shaft gear 220. As can be understood, as clamp shaft gear 220 is rotated in a clockwise direction (when viewed from the proximal end of the control handle), follower 260 will move proximally on clamp shaft gear 220. Similarly, as clamp shaft gear 220 is rotated in a counter-clockwise direction, follower 260 will move distally on clamp shaft gear 220. Follower 260 is prevented from further distal and proximal movement on clamp shaft gear 220 by stops 102, 104 formed by body 100, as can be seen in FIG. 2. Thus, stops 102, 104 and follower 260 effectively serve to prevent over-rotation in both the clockwise direction and counter-clockwise direction of gap adjust ring 210, and thus flexible gap adjust drive shaft 240. This is desirable because, as can be understood, even after gap adjust ring 210 has either completely extended the gap between the anvil head and staple firing head or completely closed the gap between the anvil head and the staple firing head, because gap adjust shaft 240 is a flexible shaft and may store torsional energy within it, gap adjust ring 210 can continue to be rotated and the torsional energy can continue to be stored within gap adjust drive shaft 240 even after the gap has been completely extended or closed. Thus, it is desirable that over-rotation of gap adjust ring 210 be prevented in both the counter-clockwise and clockwise directions. Follower 260 and stops 102, 104 provide this function.

As discussed previously, control handle 10 also includes a staple firing assembly 300. Staple firing assembly 300 is utilized to fire staples from the stapling head at the distal end of the full thickness resection device. Staple firing assembly 300 includes staple firing ring, or staple cut knob, 310, worm gear assembly 320, flexible staple drive shaft 330, and ratchet assembly 340. Each of these components will be described in further detail below.

Staple firing ring 310 is rotatably mounted on body 100 and includes gear teeth 312 on a distal, inner portion of staple firing ring 310. As will be described further later in this specification, gear teeth 312 of staple firing ring 310 engage with worm gear assembly 320. Staple firing ring 310 also includes cogs 314 on a proximal, inner portion of the staple firing ring 310. Cogs 314 receive within them locking assembly 400 in order to lock staple firing ring 310 against rotation.

As will also be discussed later in this specification, worm gear assembly 320 can be actuated in a first operative mode in response to rotation of the staple firing ring 310 in a first, or clockwise, direction. Rotation of the staple firing ring 310 in the clockwise direction actuates the worm gear assembly 320 in the first operative mode, which in-turn rotates the flexible staple drive shaft 330 in the clockwise direction. Additionally, worm gear assembly 320 can be actuated in a second operative mode. Actuation of the worm gear assembly in the second operative mode, which is opposite in motion from the first operative mode, corresponds with rotation of the flexible staple drive shaft 330 in a counter-clockwise direction. The release rate of the torsional energy that is stored in drive shaft 330 as a result of the clockwise rotation of the drive shaft is controlled by the actuation of the worm gear assembly in the second operative mode.

Actuation of the worm gear assembly in the second operative mode can be accomplished by either active rotation, i.e., rotation by the physician, of the staple firing ring 310 in the counter-clockwise direction or by simply removing a force from the staple firing ring 310 that restrains it from rotating in the counter-clockwise direction. In other words, since the flexible drive shaft 330 has torsional energy stored within it as a result of its clockwise rotation, it wants to rotate counter-clockwise unless restrained against doing so. By removing the restraining force from the staple firing ring 330, the flexible drive shaft 330 may rotate counter-clockwise but will not uncontrollably rotate because of the desirable inefficient transfer of energy in the worm gear assembly, which will also be discussed further below.

In further describing worm gear assembly 320, the assembly includes a worm pinion 322 and a worm gear coupling 324. Worm pinion 322 includes a top side 322A with gear teeth thereon and a stem portion 322B which includes threading along its length. The gear teeth on top side 322A of worm pinion 322 engage with gear teeth 312 of staple firing ring 310. Thus, as can be understood, rotation of staple firing ring 310 rotates worm pinion 322.

Staple firing ring 310 is rotated in a clockwise direction, when viewed from the proximal, or rear, end of control handle 10 in order to fire the staples from the stapling head in the distal end of the full thickness section device. Clockwise rotation of staple firing ring 310 in-turn rotates top side 322A of worm pinion 322 in a counter-clockwise direction when viewed from above. Rotation of top side 322A of worm pinion 322 also rotates threaded stem portion 322B of worm pinion 322. Threaded stem portion 322B of worm pinion 322 engages with worm gear coupling 324. Worm gear coupling 324 includes gear teeth 324A at a proximal end of worm gear coupling 324. The threaded stem 322B of worm pinion 322 engages with gear teeth 324A of worm gear coupling 324. Thus, as threaded stem portion 322B is rotated, worm gear coupling 324 is rotated in a clockwise direction when viewed from the proximal end of control handle 10.

Figure 4:
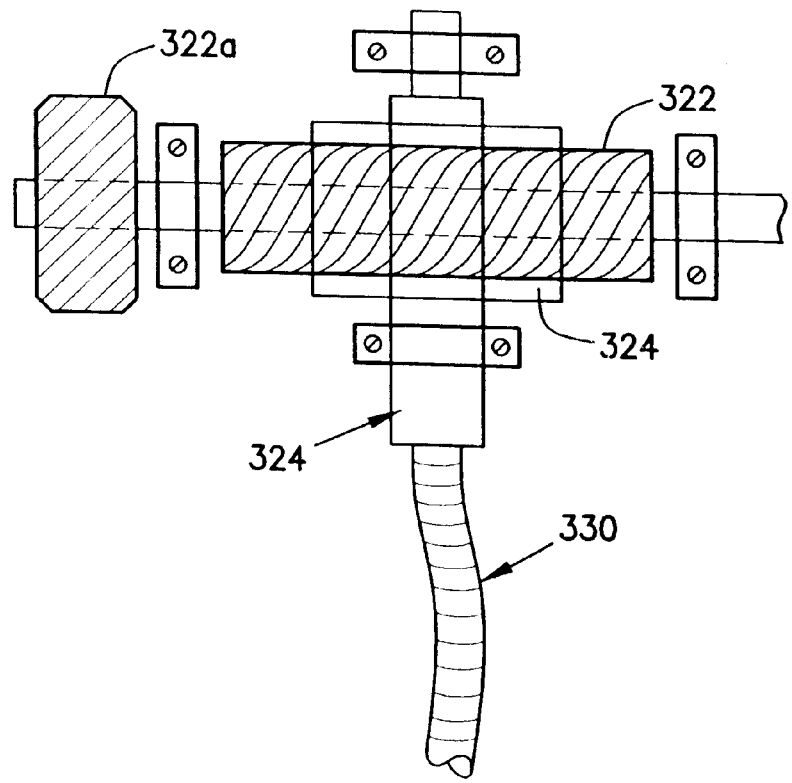
FIG. 4 is a first schematic illustration of the worm gear assembly of the present invention as viewed from a top of the assembly.

Staple drive shaft 330 is a flexible shaft that is attached at its proximal end 332 to worm gear coupling 324. Thus, as worm gear coupling 324 is rotated by worm pinion 322, flexible staple drive shaft 330 is also rotated in a clockwise direction. Because staple drive shaft 330 is a flexible drive shaft, as discussed above, it stores torsional energy within it as it is being rotated by worm gear coupling 324. FIG. 4 illustrates flexible staple drive shaft 330 after it has been rotated and with torsional energy stored within it as a result of the rotation, or winding, process.

Ratchet assembly 340 is associated with flexible staple drive shaft 330. Ratchet assembly 340 includes a ratchet 342, a pawl 344, and a ratchet/pawl cage 346. Ratchet 342 is rotatably mounted within ratchet pawl cage 346 and pawl 344 is coupled to ratchet/pawl cage 346 and is engageable with ratchet 342.

Ratchet 342 is disposed on a distal-most portion of worm-gear coupling 324. The distal end of worm gear coupling 324 includes a flat surface thereon and ratchet 342 is positioned on the distal end of worm gear coupling 324. The flat surface assists in coupling ratchet 342 on worm gear coupling 324 such that ratchet 342 will rotate with worm gear coupling 324, and thus drive shaft 330. Alternatively, ratchet 342 could be disposed on drive shaft 330.

Ratchet 342 includes teeth 342A around a portion thereof. As ratchet 342 is rotated clockwise through the firing range of the staple firing assembly 300, the pawl 344 engages with teeth 342A. Thus, during rotation through the staple firing range, ratchet 342 is able to rotate in the clockwise direction but is prevented from backward rotation in a counter-clockwise direction. Rotation through the firing range is defined as that arc of rotation that is necessary to completely fire the staples from the stapling head in the distal end of the full thickness resection device. Thus, teeth 342A of ratchet 342 are disposed around a portion of ratchet 342 such that as ratchet 342 is rotated through the firing range, pawl 344 prevents ratchet 342 from rotating in a counter-clockwise direction.

The purpose of ratchet 342 and pawl 344 is to prevent a surgeon from partially completing the staple firing sequence, i.e., not firing all of the staples, and then trying to rotate the staple firing ring 310 in a counter-clockwise direction. In other words, ratchet assembly 340 prevents a surgeon from rotating the staple firing ring 310 in a counter-clockwise direction prior to fully completing the staple firing procedure. As will be explained later, counter-clockwise rotation of the staple drive shaft 330, and thus staple firing ring 310, actuates the cutting mechanism.

Figure 5:
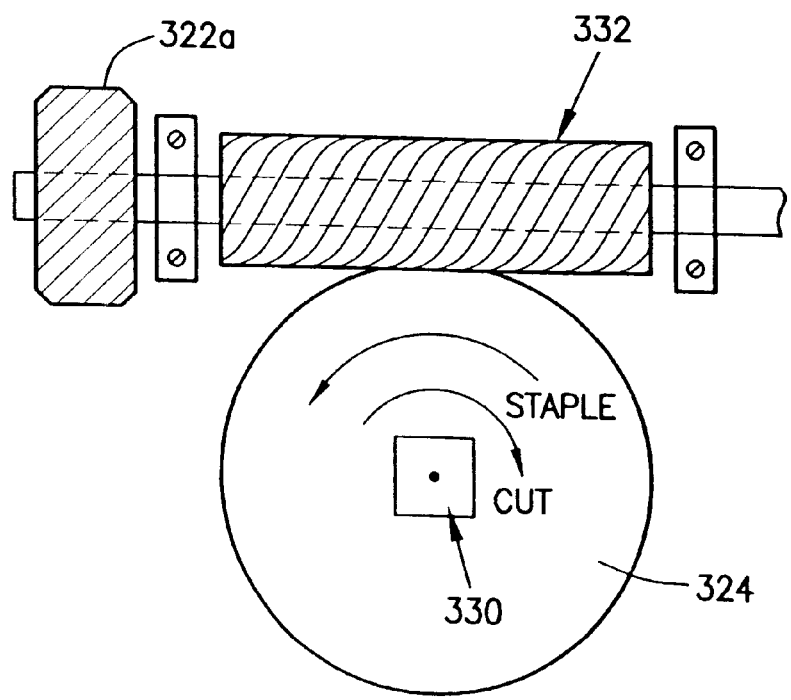
FIG. 5 is a second schematic illustration of the worm gear assembly of the present invention as viewed from a front of the assembly.

Once the staple firing procedure is complete, i.e., flexible staple drive shaft 330 has been completely rotated clockwise through the staple firing range to completely fire all of the staples in the stapling head, pawl 344 is biased away from ratchet 342. To achieve this result, pawl 344 is spring-loaded such that when it no longer engages with teeth 342A of ratchet 342, pawl 344 is biased away from ratchet 342. Thus, after the staple firing procedure has been completed, pawl 344 no longer engages with teeth 342A and staple firing ring 310 and flexible staple drive shaft 330 can be rotated in a counter-clockwise direction. As mentioned above, it is desirable that the flexible staple drive shaft 330 is rotated in a counter-clockwise direction after completion of the staple firing procedure because, after the staple firing procedure is complete, the mechanism at the distal end of the full thickness resection device that accomplishes the staple firing procedure then engages with a cutting apparatus; counter-clockwise rotation of the flexible staple drive shaft 330 rotates the cutting mechanism such that the cutting mechanism is able to cut the tissue that is to be resected. FIG. 5 illustrates the clockwise and counter-clockwise rotation of the flexible drive shaft 330.

Thus, flexible staple drive shaft 330 is rotated clockwise to complete the staple firing procedure and is rotated counter-clockwise to complete the tissue cutting procedure. It is not desirable to permit the surgeon to rotate the flexible drive shaft in a counter-clockwise direction to commence the cutting procedure until the staple firing procedure has been completed. Thus, ratchet assembly 340 prevents counter-clockwise rotation of drive shaft 330 before completion of the staple firing procedure.

As discussed previously, as flexible staple drive shaft 330 is being rotated in the clockwise direction, because the drive shaft is flexible, torsional energy is stored in the drive shaft. Once the staple firing procedure is completed, if worm gear assembly 320 was not present in control handle 10, the torsional energy stored in flexible drive shaft 330 would cause the drive shaft to uncontrollably unwind in the counter-clockwise direction during the tissue cutting procedure. It is not desirable to have uncontrolled rotation of drive shaft 330 as a result of the release of the torsional energy in the flexible drive shaft. Thus, worm gear assembly 320 provides for a controlled release of the torsional energy in flexible drive shaft 330 due to the gearing mechanism described above of worm gear assembly 320.

Worm gear assembly 320 is designed to inefficiently transfer energy between worm gear coupling 324 and worm pinion 322. It is this inefficient transfer of energy in the worm gear assembly 320 that provides for a controlled release of the torsional energy that is stored in the flexible staple drive shaft 330. The threaded stem 322B of worm pinion 322 and the gear teeth 324A of worm gear coupling 324 provide for this inefficient transfer of energy between the worm pinion 322 and the worm gear coupling 324. As described previously, worm pinion 322 is rotated about a first axis and worm gear coupling 324 is rotated about a second axis with the first axis being perpendicular to the second axis.

Control handle 10 also includes locking assembly 400. As described previously, and as will be further described below, locking assembly 400 alternatively locks gap adjust ring 210 and staple firing ring 310 against further rotation. Thus, in the present invention, either gap adjust ring 210 or staple firing ring 310 can be rotated while the other of the rings is locked-out against rotation. Thus, the surgeon is able to either adjust the gap or fire the staples and is not able to do both procedures simultaneously. In this manner, a safety mechanism is provided for the surgeon to ensure that only one of the procedures is accomplished at any particular time.

Locking assembly 400 includes a shuttle 410 and a button beam 420. Shuttle 410 is slidably disposed within transition piece 250. Shuttle 410 includes a first tab 412 and a second tab 414. First tab 412 and second tab 414 are both capable of being extended beyond transition piece 250 such that they are able to be received within one of cogs 214 of gap adjust ring 210 or cogs 314 of staple firing ring 310, respectively.

A top portion of shuttle 410 is disposed within button beam 420. Button beam 420 is utilized to slidably move shuttle 410 within transition piece 250 such that shuttle 410 is able to engage with one of the gap adjust ring 210 or the staple firing ring 310.

As discussed above, shuttle 410 is slidably disposed within transition piece 250. In order to lock gap adjust ring 210 against further rotation, button beam 420 is moved proximally such that shuttle 410 is also moved proximally. In this proximal position for shuttle 410, second tab 414 is received within one of cogs 214 in gap adjust ring 210. As can be understood, when second tab 414 of shuttle 410 is received within one of the cogs 214, gap adjust ring 210 can no longer be rotated in either the clockwise or the counter-clockwise direction. Additionally, when tab 414 is received within one of cogs 214, tab 412 is not received within one of cogs 314. In order to lock staple firing ring 310 against further rotation, button beam 420 is moved distally which in-turns moves shuttle 410 distally. In this distal position for shuttle 410, first tab 412 of shuttle 410 is received within one of cogs 314 in staple firing ring 310. As can also be understood, when first tab 412 is received within one of cogs 314 in staple firing ring 310, staple firing ring 310 is prevented from further rotation in either the clockwise or the counter-clockwise directions. When tab 412 is received within one of cogs 314, tab 414 is not received within one of cogs 214.

As can be seen in FIG. 2, a biasing spring 416 is included within shuttle 410 which biases both first tab 412 and second tab 414 in an outward direction from shuttle 410. This is desirable in order to ensure secure positioning of the tabs within one of the respective cogs of either the gap adjust ring 210 or the staple firing ring 310.

In practicing a method of the present invention, a method for actuating a full thickness resection device includes the steps of rotating a staple firing ring and rotating a worm gear assembly, where the worm gear assembly is coupled to the staple firing ring. A flexible drive shaft is rotated where the flexible drive shaft is coupled to the worm gear assembly.

In practicing another method of the present invention, a method for actuating a full thickness resection device includes the steps of rotating a staple firing ring in a first direction. A worm gear assembly is actuated in a first operative mode in response to the rotation of the staple firing ring in the first direction. The worm gear assembly is coupled to the staple firing ring. A flexible drive shaft is rotated in the first direction where the flexible drive shaft is coupled to the worm gear assembly. Torsional energy is stored in the flexible drive shaft during rotation of the flexible drive shaft in the first direction. Additionally, the worm gear assembly is actuated in a second operative mode. A release rate of the stored torsional energy in the flexible drive shaft is controlled by the worm gear assembly. The flexible drive shaft is rotated in a second direction.

Above, the step of actuating the worm gear assembly in the first operative mode may include the steps of rotating the worm pinion on a first axis, where the worm pinion is engaged with the worm gear coupling, and rotating the worm gear coupling on a second axis. The first axis is perpendicular to the second axis.

The disclosed embodiments are illustrative of the various ways in which the present invention may be practiced. Other embodiments can be implemented by those skilled in the art without departing from the spirit and scope of the present invention.

What is claimed is:
1. A control handle for a full thickness resection device, comprising:
   a body; and
   a staple firing assembly coupled to the body, the staple firing assembly including;

a rotatable staple firing ring;

a worm gear assembly coupled to the staple firing ring; and a flexible drive shaft coupled to the worm gear assembly.

2. The control handle for a full thickness resection device of claim 1 wherein the staple firing assembly further includes a ratchet assembly coupled to the flexible drive shaft.

3. The control handle for a full thickness resection device of claim 1 wherein the rotatable staple firing ring includes gear teeth on an inner portion of the staple firing ring and wherein the worm gear assembly includes a worm pinion having gear teeth on a top side thereof, the gear teeth of the staple firing ring engaged with the gear teeth of the worm pinion.

4. The control handle for a full thickness resection device of claim 3 wherein the worm gear assembly further includes a worm gear coupling having gear teeth, the gear teeth of the worm gear coupling engaged with a threaded stem portion of the worm pinion.

5. The control handle for a full thickness resection device of claim 4 wherein the flexible drive shaft is coupled to the worm gear coupling.

6. The control handle for a full thickness resection device of claim 2 wherein the ratchet assembly includes:

a cage rigidly coupled to the body;

a ratchet rotatably coupled to the cage, the ratchet having teeth around a portion thereof; and a pawl coupled to the cage and engageable with the teeth of the ratchet.

7. The control handle for a full thickness resection device of claim 1 further comprising a gap adjustment assembly coupled to the body.

8. The control handle for a full thickness resection device of claim 7 wherein the gap adjustment assembly includes:

gap adjustment ring, the gap adjustment ring including gear teeth on an inner portion of the gap adjustment ring;

a clamp shaft gear having gear teeth, the clamp shaft gear teeth engaged with the gear teeth on the inner portion of the gap adjustment ring;

a spur gear having teeth, the spur gear teeth engaged with the clamp shaft gear teeth; and a flexible gap adjust drive shaft attached to the spur gear.

9. The control handle for a full thickness resection device of claim 8 wherein the gap adjustment assembly further includes:

a follower, wherein the follower is threadedly engaged with a threaded shaft of the clamp shaft gear.

10. The control handle for a full thickness resection device of claim 9 wherein the follower includes a scallop and wherein the flexible gap adjust drive shaft is positioned within the scallop.

11. The control handle for a full thickness resection device of claim 8 further comprising a transition ring disposed between the gap adjustment ring and the staple firing ring and wherein the transition ring defines a slot on an inner portion thereof, the spur gear disposed through the slot.

12. The control handle for a full thickness resection device of claim 8 further comprising a locking assembly, the locking assembly including:

a button beam slidable within the body; and a shuttle having a first tab and a second tab attached to the button beam;

wherein the staple firing ring includes a plurality of cogs on an inner portion of the staple firing ring and the gap adjustment ring includes a plurality of cogs on the inner portion of the gap adjustment ring and wherein the first tab is engageable with one of the plurality of cogs on the inner portion of the staple firing ring and the second tab is engageable with one of the plurality of cogs on the inner portion of the gap adjustment ring.

13. The control handle for a full thickness resection device of claim 8 wherein the clamp shaft gear defines an aperture extending therethrough.

14. A method for actuating a full thickness resection device, comprising the steps of:

rotating a staple firing ring;

rotating a worm gear assembly, the worm gear assembly coupled to the staple firing ring; and rotating a flexible drive shaft, the flexible drive shaft coupled to the worm gear assembly.

15. The method of claim 14 wherein the worm gear assembly includes:

a worm pinion having gear teeth on a top side thereof engaged with gear teeth of the staple firing ring; and a worm gear coupling having gear teeth, the gear teeth of the worm gear coupling engaged with a threaded stem portion of the worm pinion.

16. The method of claim 15 wherein the worm pinion is mounted 90 degrees to the worm gear coupling.

17. The method of claim 14 wherein the step of rotating the worm gear assembly includes the steps of:

rotating a worm pinion on a first axis, the worm pinion engaged with a worm gear coupling; and rotating the worm gear coupling on a second axis;

wherein the first axis is perpendicular to the second axis.

18. A method for actuating a full thickness resection device, comprising the steps of:

rotating a staple firing ring in a first direction;

actuating a worm gear assembly in a first operative mode in response to the rotation of the staple firing ring in the first direction, the worm gear assembly coupled to the staple firing ring;

rotating a flexible drive shaft in the first direction, the flexible drive shaft coupled to the worm gear assembly, wherein torsional energy is stored in the flexible drive shaft during rotation of the flexible drive shaft in the first direction;

actuating the worm gear assembly in a second operative mode;

controlling a release rate of the stored torsional energy in the flexible drive shaft by the worm gear assembly; and rotating the flexible drive shaft in a second direction.

19. The method of claim 18 wherein the step of actuating the worm gear assembly in the first operative mode includes the steps of:

rotating a worm pinion on a first axis, the worm pinion engaged with a worm gear coupling; and rotating the worm gear coupling on a second axis;

wherein the first axis is perpendicular to the second axis.

20. The method of claim 18 wherein the worm gear assembly includes:

a worm pinion having gear teeth on a top side thereof engaged with gear teeth of the staple firing ring; and a worm gear coupling having gear teeth, the gear teeth of the worm gear coupling engaged with a threaded stem portion of the worm pinion.

21. The method of claim 20 wherein the worm pinion is mounted 90 degrees to the worm gear coupling.

* * * * *